United States Patent [19]

Kodachi et al.

[11] Patent Number: 4,857,164
[45] Date of Patent: Aug. 15, 1989

[54] OXYGEN ANALYZER

[75] Inventors: Toru Kodachi, Nagoya; Jun Usami, Aichi, both of Japan

[73] Assignee: NGK Insulators, Ltd., Nagoya, Japan

[21] Appl. No.: 107,397

[22] Filed: Oct. 13, 1987

[30] Foreign Application Priority Data

Oct. 16, 1986 [JP] Japan .................................. 61-244038
Nov. 7, 1986 [JP] Japan .................................. 61-264099

[51] Int. Cl.⁴ ............................................. G01N 27/58
[52] U.S. Cl. .................................................... 204/406
[58] Field of Search ............... 204/406, 410, 412, 425, 204/1 S

[56] References Cited

U.S. PATENT DOCUMENTS

| 4,601,809 | 7/1986 | Kitahara | 204/406 |
| 4,622,126 | 11/1986 | Shimomura | 204/425 |
| 4,706,637 | 11/1987 | Asakura et al. | 123/589 |
| 4,707,241 | 11/1987 | Nakagawa et al. | 204/406 |

Primary Examiner—G. L. Kaplan
Attorney, Agent, or Firm—Arnold, White & Durkee

[57] ABSTRACT

An oxygen analyzer using an oxygen sensor by which the oxygen concentration of a measuring gas can be detected. The oxygen sensor includes an oxygen pump and an oxygen concentration cell. The detecting principle is to vary the reference voltage to be compared with an output electromotive force of the oxygen concentration cell by using a predetermined relationship between the electromotive force and the pumping current, thus eliminating the need of using a reference air of which oxygen concentration is compared as a reference.

5 Claims, 8 Drawing Sheets

FIG_1

FIG_2

FIG_3A

FIG_3B

FIG_4

FIG_5

FIG_6

FIG_7

FIG_8

FIG. 9
PRIOR ART

FIG_10
PRIOR ART

OXYGEN ANALYZER

BACKGROUND OF THE INVENTION

1. Field of the Invention

The present invention relates in general to an oxygen analyzer of an industrial purpose and more particularly to an industrial oxygen analyzer for detecting oxygen concentration in a combustion exhaust gas in an industrial furnace or boiler or an exhaust gas passageway or in an atmosphere.

2. Related Art Statement

Such a device has been disclosed in the specification of Japanese patent application No. Sho-61-202382 (1986). The detecting principle of the oxygen concentration of said known device will be explained first by referring to a simplified diagram shown in FIG. 9.

Figure 9:
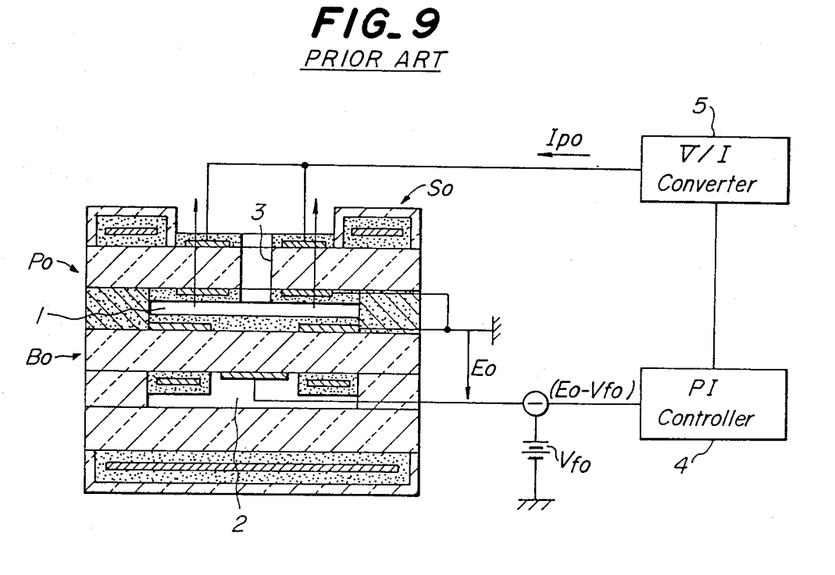
FIGS. 9 and 10 show a prior art device in partial cross-sectional view and a diagram.

An oxygen sensor or sensing element $S_o$ for detecting the oxygen concentration of a measuring gas comprises a diffusion chamber 1 in which the measuring gas is introduced by diffusion, an oxygen pumping portion $P_o$ and an oxygen concentration cell portion $B_o$ being arranged to surround said diffusion chamber, and an air passageway 2 communicating to the outer atmosphere.

The oxygen concentration cell portion $B_o$ compares the measuring gas introduced into the diffusion chamber 1 through a gas introducing hole 3 provided in the oxygen pumping portion $P_o$ with an atmospheric air being a reference air introduced through the air passageway 2 and produces an electromotive force $E_o$ in response to the ratio of the oxygen partial pressure thereof. The produced electromotive force $E_o$ is compared with a reference voltage $V_{f0}$ (an electromotive force of about 400 mV corresponding to air ratio $m \simeq 1$). The deviation or the difference voltage ($E_o - V_{f0}$) therebetween is supplied to a PI (proportional integration) controller 4 for controlling the pumping current $I_{P0}$ of the oxygen pumping portion $P_o$ so as to compensate said difference or deviation. Since the output of the PI controller 4 is a voltage signal, such a voltage signal is first supplied to a voltage-to-current (V/I) converter 5 and converted into a current amount which is used as the desired pumping current $I_{p0}$.

The PI controller 4 acts to control the amount of the pumping current $I_{P0}$ through the V/I converter 5 so as to pump out the oxygen in the diffusion chamber 1 by the oxygen pumping portion P according to said deviation ($E_o - V_{f0}$). By this control, the oxygen concentration in the diffusion chamber 1 is maintained at 0.002 ppm which corresponds to an air ratio $m \simeq 1$.

Accordingly, the oxygen concentration of the measuring gas is co-related to the amount of the pumping current $I_{P0}$ and by using this relationship, the oxygen concentration of the measuring gas is obtained.

Figure 10:
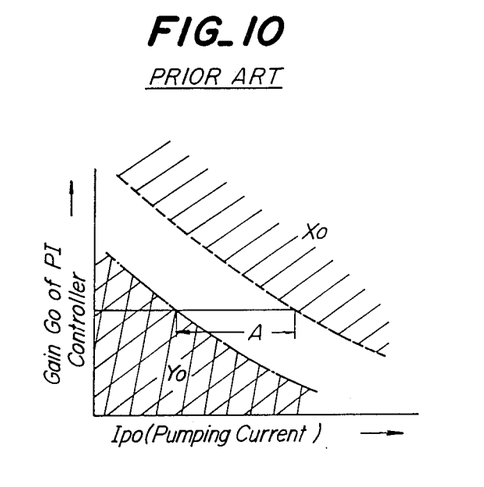

The relation between the gain $G_o$ of the PI controller 4 and the amount of the pumping current $I_{P0}$ is given by a diagram shown in FIG. 10. As can be seen from the diagram, there is an oscillating region $X_o$ shown by hatching and an overshooting region $Y_o$ shown by cross-hatching. In both these regions $X_o$ and $Y_o$ in the previous system, stable and accurate measurement of the oxygen concentration of the measuring gas could not be carried out.

PROBLEMS SOLVED BY THE PRESENT INVENTION

In summary, the conventional devices have the following disadvantages.

(1) Reference gas is required when detecting the oxygen concentration of the measuring gas so that an air passageway 2 communicating to the atmospheric air is inevitable. This imposes restriction for the freedom in the design of the measuring device.

(2) The PI (preportional integration) controller 4 is used under a condition that the gain factor G is constant so that the range of the current amount of the pumping current $I_{P0}$ for stable and accurate measurement is limited to the region A as shown in FIG. 10. Accordingly, there has been a problem that the measurement range of the oxygen concentration is limited to a narrow range, for instance, oxygen concentration x% to y% only.

SUMMARY OF THE INVENTION

The present invention has for its object to solve the aforementioned problems in the conventional devices.

MEASURES FOR SOLVING THE PROBLEMS

According to the present invention, the oxygen analyzer for industrial purpose has its feature in that it comprises;

a diffusion chamber in which measuring gas is diffused, an oxygen concentration cell and detecting means having an oxygen pump arranged to surround the diffusion chamber, setting voltage means for setting a reference voltage to be compared with an electromotive force produced from said oxygen concentration cell, controlling means for controlling current amount of pumping current of the oxygen pump based on a deviation obtained by the comparison of the electromotive force and the reference voltage, and for detecting an oxygen concentration of the measuring gas having correlation with the current amount of the pumping current, wherein the reference voltage is so varied by the setting voltage means based on a predetermined mutual relationship between the electromotive force produced from the oxygen concentration cell at a predetermined oxygen concentration in the diffusion chamber and the current amount of said pumping current that the reference voltage becomes equal to said electromotive force of the oxygen concentration cell corresponding to the current amount of the pumping current based on a variation of the amount of the pumping current by said mutual relationship.

Furthermore, the invention has its additional feature in that the controlling means comprises means for decreasing the gain according to the current amount of the pumping current.

FUNCTION (1) The reference voltage is varied according to a predetermined mutual relationship between the electromotive force of the oxygen concentration cell at a predetermined oxygen concentration in the diffusion chamber and the current amount of the pumping current. Thus when an equilibrium is attained, the oxygen concentration in the diffusion chamber reaches a predetermined concentration. Accordingly, the current amount of the pumping current is decided based on the difference between the abovementioned predetermined concentration and the oxygen concentration of the measuring gas.

Thus, for example, if the predetermined oxygen concentration is made an oxygen concentration of 0.002 ppm an air ratio m≈1, the difference between the oxygen concentration 0.002 ppm and that X ppm of the measuring gas, i.e.;

(X−0.002) ppm is an amount to derive the amount of current of the pumping current and the oxygen concentration X ppm of the measuring gas is obtained from the above correlation.

(2) Since the gain is reduced according to the current amount of the pumping current, a relationship between the gain of the PI (proportional integration) controller and the current amount of the pumping current is obtained which covers outside the oscillation region and zones along the oscillation region.

BRIEF DESCRIPTION OF THE DRAWINGS

FIGS. 1 to 6 are the drawings for explaining a practical embodiment of an industrial oxygen analyzer of the present invention, in which:

PREFERRED EMBODIMENT OF THE INVENTION

A practical embodiment of the industrial oxygen analyzer of the present invention will be explained by referring to the accompanying drawings.

Figure 1:
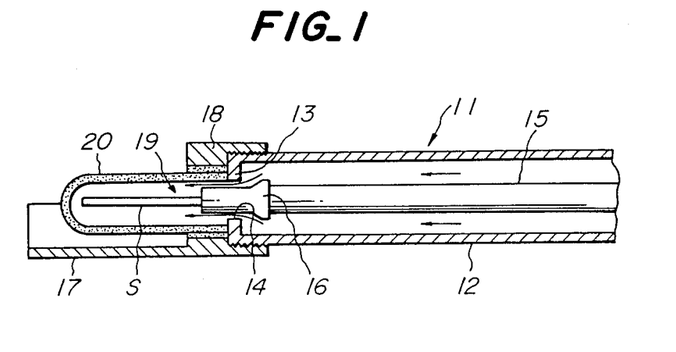
FIG. 1 is a general view in cross-section.

As can be seen from FIG. 1, a probe 11 for collecting the combustion exhaust gas, which in this case being the gas to be measured, is arranged by inserting it into an opening of a furnace wall (not shown) of a flue of a combustion furnace. The probe 11 comprises an oxygen sensor or sensing element S for detecting the oxygen concentration in the combustion exhaust gas.

The probe 11 comprises a closed top cylindrical outer tube 12 extending laterally in the drawing and formed of heat resistive metal such as SUS and the like. In the bottom wall 13 of the outer tube 12 located at the left end in the drawing, a circular hole 14 is provided. A connector 16 is loosely fitted in the hole 14. This connector 16 is coupled to the oxygen sensing element S by inserting it at the left side and to sheath lead 15 formed of heat resistive material such as *Inconel* coupled at the right hand side.

At the left end side of the outer tube 12, a ring shaped filter supporting member 18 is thread coupled thereon.

A dust screen 17 extending to the left side is secured to the supporting member 18. The filter supporting member 18 supports a dust proof ceramic filter 20 at its hollow portion 19. As can be seen from the drawing, the oxygen sensing element S and a part of the connector 16 are housed in the hollow portion 19. Namely these members like the oxygen sensing element S are protected by the ceramic filter 20. This ceramic filter 20 is made from porous material and is hermetically secured to the filter supporting member 18 by alumina cement or the like. The dust screen 17 shields the ceramic filter 20 against direct communication with the combustion exhaust gas so as to prevent stacking of dust on the ceramic filter 20.

Figure 2:
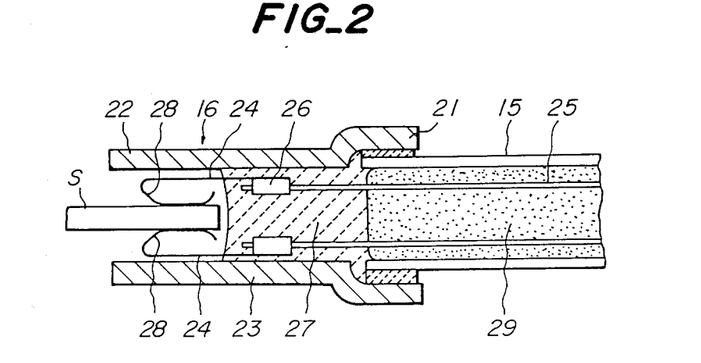
FIG. 2 is a partial enlarged view of FIG. 1.

The connector 16 is as shown in a more detailed view in FIG. 2 and comprises a cylindrical member 23 made of a low temperature sintered ceramic having a large diameter portion 21, a small diameter portion 22 and a terminal structure having a plurality of terminal members 24. Each of the terminal members 24 is secured at its connecting portion 26 and electrically connected to a nickel wire 25 against the cylindrical member 23 by embedding it into water glass. The terminal members 24 are formed of heat resistive elastic members having good electrical conductivity and having contact portions 28. By inserting one end of the oxygen sensing element S between the contact portions 28, the oxygen sensing element S is secured in its position and is electrically connected. Inside the large diameter portion 21 of the cylindrical member 23, the left end of the cylindrical sheath lead 15 having the abovementioned nickel wires 25 passing through its hollow portion is coupled and hermetically jointed by alumina cement or the like against the cylindrical member 23. In the hollow portion of the sheath lead 15, magnesium oxides 29 are filled in order to prevent mutual contact of the nickel wires 25.

The calibration gas is introduced into the hollow space of the ceramic filter 20 through the hollow portion of the outer tube 12 and through a clearance in the hole 14 in the bottom wall 13 of the outer tube 12 located between the connector 16 as shown by the arrows in FIG. 1.

As has been explained in the foregoing, the sheath lead 15 and the connector 16 are formed integrally so that a simple construction is obtained and miniaturization of the device can be achieved. Moreover, the assembling can also be simplified. Additionally, since the oxygen sensing element S is arranged detachably with the connector 16, the exchange of the sensing element S can be carried out very easily.

Construction of the oxygen sensing element S having the size of about 5 mm (width)×1.0 mm (thickness)×30~60 mm (length) will be explained with respect to FIGS. 3A and 3B and FIG. 4 hereinafter.

Figure 3A:
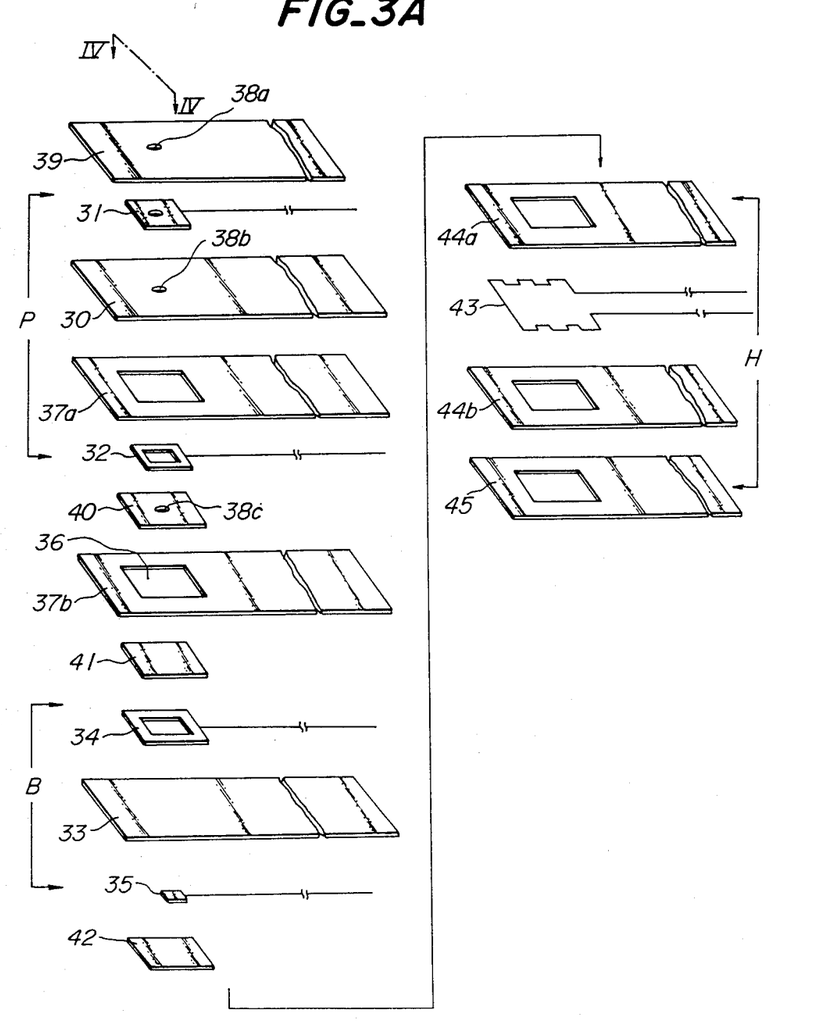
FIG. 3A is an exploded view of an oxygen sensing element.
Figure 3B:
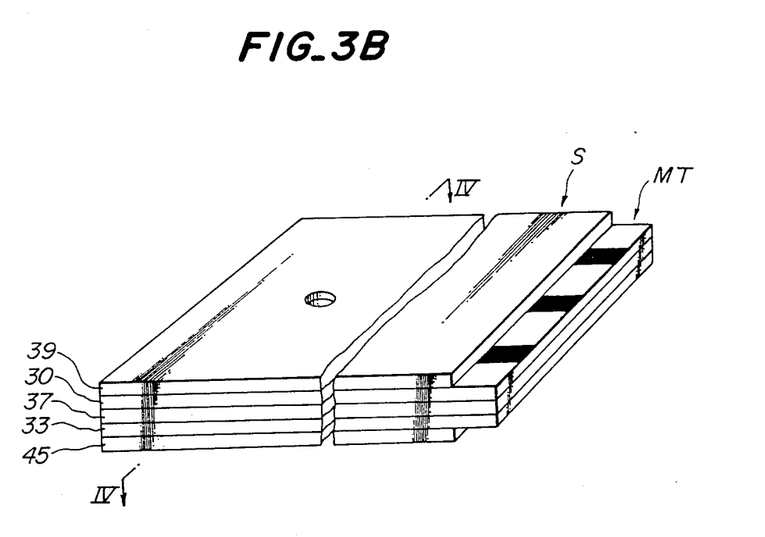
FIG. 3B is a general perspective view thereof.

At an upper side of the oxygen sensing element S shown in FIGS. 3A and 3B, there is provided an oxygen pumping portion P comprising a solid electrolyte element 30, an upper pumping electrode 31 and a lower pumping electrode 32 being arranged at upper and lower sides of the solid electrolyte element 30, respectively.

In the middle portion of the element S, in a similar manner with the abovementioned oxygen pumping portion P, an oxygen concentration cell portion B is provided. The call portion B comprises a solid electrolyte member 33, and an upper cell electrode 34 and a lower cell electrode 35 arranged at upper and lower sides of the solid electrolyte element 33, respectively.

Between the oxygen pumping portion P and the oxygen concentration cell portion B, a spacer member 37 (37a, 37b) formed of an insulator having a certain thickness is interposed to form a diffusion chamber 36 in the shape of a narrow flat space into which the measuring gas is introduced with a predetermined diffusion resistance. At the center position of the diffusion chamber 36 in the oxygen pumping portion P, a gas introducing hole 38 (38a, 38b, 38c) is provided for communicating the diffusion chamber 36 to the outer space in which the measuring gas exists.

The measuring gas is introduced through this gas introducing hole 38 (38a, 38b, 38c) into the diffusion chamber 36 and diffused in the diffusion chamber 36 under a certain diffusion resistance and comes in contact with the lower pumping electrode 32 of the oxygen pumping portion P. The measuring gas also comes in contact with the upper cell electrode 34 of the oxygen concentration cell portion B at a location near said lower pumping electrode 32. The upper pumping electrode 31 of the oxygen pumping portion P and also the lower cell electrode 35 of the oxygen concentration cell portion B are both facing to the outer space in which the measuring gas exists and thus, these electrodes directly contact the measuring gas.

At the lower side of the element, a heater portion H is provided to heat the oxygen pumping portion P and the oxygen concentration cell portion B to a predetermined temperature, for instance, over 600° C.

The solid electrolyte members 30 and 33 are made of stabilized or partially stabilized zirconia ceramics which exhibit oxygen ion conductivity at high temperatures. As is known in the art, these stabilized or partially stabilized zirconia ceramics may be obtained by forming a solid solution of zirconium oxide with yttrium oxide, calcium oxide, and the like. Each of the electrodes 31, 32, 34 and 35 may be formed of porous platinum, and the like. Over each of these electrodes 31, 32, 34 and 35, respective porous ceramic layers 39, 40, 41 and 42 made of alumina, and the like, are provided in a laminated manner. Accordingly, the measuring gas comes in contact with these electrodes 31, 32, 34 and 35 through the respective porous ceramic layers 39, 40, 41 and 42.

The heater member H is provided in a form that the heater element 43 is covered by a porous layer 44 (44a, 44b) formed of alumina and the like, and exhibits insulating properties. Surrounding the porous layer 44 is an air-tight layer 45 formed of solid electrolyte such as zirconia. By this air-tight layer 45, the heater element 43 is separated or isolated from the outer measuring gas. The heater element 43 may be formed, for instance, by printing using paste having the main content of mixture of alumina powder and platinum powder or by arranging a cermet like film on a base.

Figure 4:
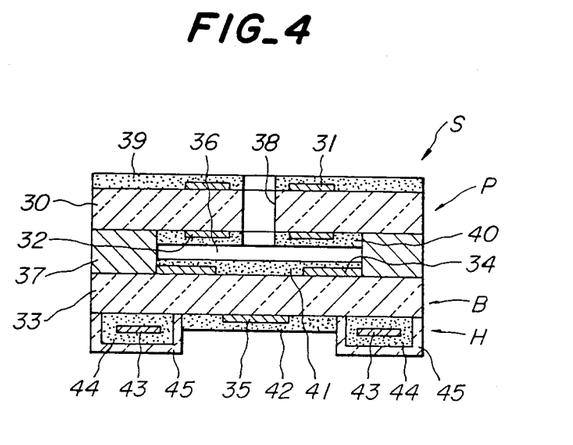
FIG. 4 is a cross-sectional view taken along line IV—IV in FIGS. 3A and 3B.

The abovementioned oxygen pumping portion P, the oxygen concentration cell portion B, the heater portion H and the spacer member 37 (37a, 37b) are laminated to form an elongated plate shape body as shown in FIG. 4 and then sintered to form a unitary construction.

A printed contact terminal MT (FIG. 3-B) is provided with the oxygen sensing element S for connecting the pumping electrodes 31 and 32, cell electrodes 34 and 35, and the heater element 43. The terminal MT completes the required electric connection to the outer measuring circuit which will be explained hereinafter by inserting the element S between the contact portions 28, 28 of the terminal members 24.

When measuring the oxygen concentration, a heater current is passed through the heater element 43 and the detection is commenced at a time when the oxygen pumping portion P and the oxygen concentration cell portion B are heated over a predetermined temperature. It takes about 2 minutes until the oxygen sensing element S reaches the predetermined temperature from the starting time of the conduction of the heater current. The required power consumption is about 6 W.

Operation of the device will be explained hereinafter by referring to a block diagram shown in FIG. 5.

The oxygen concentration cell portion B compares the measuring gas in the diffusion chamber 36 introduced therein by diffusion through the gas introducing hole 38 and that located in the outer space and produces an electromotive force E corresponding to a ratio of partial oxygen pressure thereof between the cell electrodes 34 and 35. The produced electromotive force E is compared with a reference voltage $V_f$ in a setting voltage portion 50. The difference voltage $(E - V_f)$ is supplied to a PI (proportional integration) controlling portion 51 which controls the current amount of the pumping current $I_P$ of the oxygen pumping portion P. The PI controlling portion 51 effects proportional integration control and produces a predetermined voltage signal to compensate said deviation or difference $(E - V_f)$ quickly. This voltage signal derived from the PI controlling portion 51 is supplied to a voltage-to-current (V/I) converter portion 52 comprising an attenuator 54 and a V/I converter 55 and is converted into a current amount of the pumping current $I_P$ in a predetermined form.

The reference voltage $V_f$ of the setting voltage portion 50 is set by the following manner.

The oxygen concentration of the measuring gas in the diffusion chamber 36 is assumed at a predetermined concentration of 0.002 ppm at air ratio $m \simeq 1$. By using the following Nernst's equation the calculation is carried out.

$$E_c = \frac{R \cdot T}{n \cdot F} \, en\left(\frac{P_{O2}}{P_{O2}'(= 0.002 \text{ ppm})}\right)$$

Wherein;
R: gas constant
T: absolute temperature
F: Faraday's constant
$P_{O2}$: oxygen concentration of measuring gas at outside of the oxygen sensing element
$P_{O2}'$: oxygen concentration of measuring gas at inside the diffusion chamber Namely, the mutual relationship between the electromotive force $E_c$ of the oxygen concentration cell portion and the current amount of the pumping current $I_P$ is calculated while assuming the oxygen concentration $P_{O2}$ of the measuring gas in the diffusion chamber 36 to be a predetermined value of 0.002 ppm.

Figure 6:
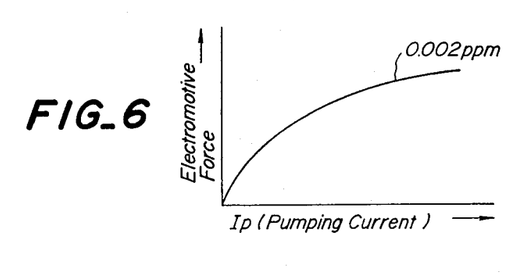
FIG. 6 is a diagram showing the relationship between the electromotive force $E_c$ of the oxygen concentration cell and the current amount $I_P$ of the pumping current at a predetermined oxygen concentration of the measuring gas.

This relationship is depicted in the diagram as shown in FIG. 6. The current amount of the pumping current $I_P$ can be obtained by using the difference between the oxygen concentration $P_{O2}$ of the measuring gas at outside of the sensing element S and the oxygen concentration $P_{O2}'$ of the measuring gas in the diffusion chamber 36.

From the abovementioned mutual relationship, the voltage value of the reference voltage $V_f$ is set in a manner that it corresponds to an electromotive force $E_c$ which represents the variation of current amount of the pumping current $I_P$ delivered from the V/I converter portion 52, or more practically corresponding to the voltage signal appearing at the output of the PI controlling portion 51.

At the beginning of the oxygen analysis when the amount of the pumping current is zero, the reference voltage $V_f$ is set other than value zero irrespective to the aforementioned mutual relationship in order to initiate the operation of the system. This value is set, for instance, at a voltage value of +5 mV.

By the above operation, the oxygen concentration of the measuring gas in the diffusion chamber 36 is maintained at 0.002 ppm by the control of the PI controlling portion 51 for the pumping current $I_P$ according to the deviation $(E-V_f)$ and the control of pumping off amount of the oxygen in the diffusion chamber to the outside is effected. The above maintained condition of the oxygen concentration is in an equilibrium condition, in which the amount of introduction of the measuring gas into the diffusion chamber 36 is equal to the amount of pumping out of the oxygen in the diffusion chamber to the outside. Accordingly, the pumping out amount, in other words, the amount of the pumping current $I_P$, is in proportion to the oxygen concentration of the measuring gas so that the oxygen concentration is detected by means of the amount of the pumping current.

The output voltage signal for controlling the pumping current $I_P$ derived from the PI (proportional integration) controlling portion 51 is also supplied to an output converter portion 53 consisting of a linearizer 58 and an output converter 59, and an output signal is derived therefrom as an analyzing signal for detecting the oxygen concentration in the measuring gas being correlated to the amount of the pumping current.

As the method of obtaining the electromotive force corresponding to the current amount of the pumping current $I_P$ in the setting voltage portion 50 by using the mutual relationship between the electromotive force $E_c$ of the oxygen concentration cell and the current amount of the pumping current $I_P$, the followings are considered.

(1) Means of digital calculation based on Nernst's formula.

(2) Means to read out from a memory in which the corresponding numerical values are stored.

(3) Analog means such as contraction, tangent line, and approximation circuit or the like realized by combining resistors and diodes, etc.

In the above embodiment, the mutual relationship between the electromotive force $E_c$ and the current amount of the pumping current $I_P$ is derived under a certain constant oxygen concentration (0.002 ppm). However, it is also possible to set different oxygen concentration for each section of the device and to derive the relationship. In this case, the oxygen concentration of the measuring gas should be derived from the output signal of the output converter portion 53 under differently set oxygen concentration.

In the above embodiment, the mutual relationship is calculated from the Nernst's equation. But it is also possible to obtain directly from experiments or the like.

The term of "electromotive force" used in this specification should be understood to include a corresponding value for the electromotive force.

Figure 5:
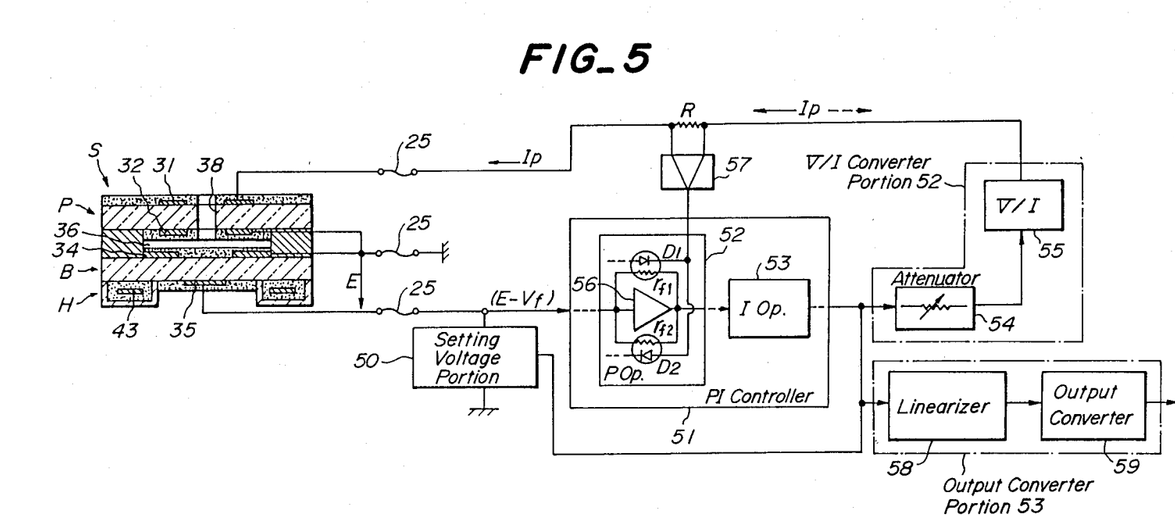
FIG. 5 is a block diagram of the analyzer.
Figure 7:
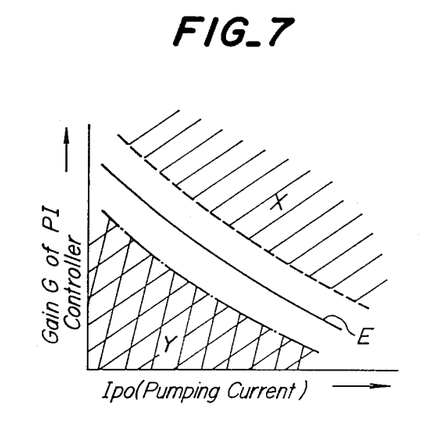
FIG. 7 is a diagram for showing the relationship between the gain G of the PI (proportional integration) controller and the current amount of the pumping current.

As can be seen from the block diagram of FIG. 5, the amplifier stage 56 of the proportional operation controlling circuit 52 of the PI controlling portion 51 comprises cadmium resistors $r_{f1}$ and $r_{f2}$ in each of the pair of the feed-back circuits provided with this amplifier stage 56. Against each of the cadmium resistors $r_{f1}$ and $r_{f2}$, photodiodes $D_1$ and $D_2$ optically coupled thereto are connected respectively in an opposite sense as shown in the drawing. Namely, the photodiodes $D_1$ and $D_2$ are connected oppositely in positive and negative directions of the pumping current $I_P$. To these photodiodes $D_1$ and $D_2$, a current obtained from a voltage drop across a resistor R included in the pumping current $(I_P)$ path and via an amplifier 57 is supplied. This current is in proportion to the current amount of the pumping current $I_P$. By this arrangement, the gain G of the PI controlling portion 51 is decreased in accordance with the negative resistance characteristics of the cadmium resistors $r_{f1}$ and $r_{f2}$. Thus, the gain G is decreased depending on the current amount of the pumping current $I_P$ and a gain curve E as shown in FIG. 7 can be obtained.

By this arrangement, the controllable range of current amount of the pumping current $I_P$ can be made wider. In FIG. 7, the hatched portion X is the oscillation region and the cross-hatched region Y is the overshooting region.

It can be understood that the oscillation phenomena can be suppressed over a wider range of the pumping current $I_P$ and thus the measurement range of the oxygen concentration becomes wider.

Figure 8:
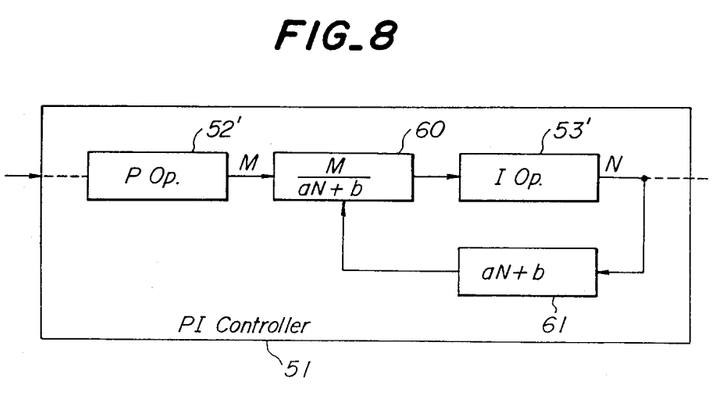
FIG. 8 is a block diagram for explaining a modified embodiment of the invention.

A modified embodiment of the present invention will be explained by referring to FIG. 8.

A difference in this modified embodiment is the provision of a division circuit 60 between the proportional operation circuit 52' and the integration operation circuit 53'. In this division circuit 60, the output M of the proportional operation circuit 52' is divided by the output N of the integration operation circuit 53' through a coefficient setting circuit 61. In the coefficient setting circuit 61, the output N of the integration operation circuit 53' is modified to include constants and to change it into a form of (aN+b) for instance, wherein a and b are constants so that an infinite value as the result of division is avoided. The output of the division circuit 60 is supplied to the integration operation circuit 53'.

In this construction, by using the output of the integration operation circuit 53', which is in proportion to the current amount of the pumping current $I_P$, or in other words by the output of the PI controlling portion 51', the gain is decreased in accordance with the current amount of the pumping current $I_P$.

EFFECT OF THE INVENTION

In accordance with the present invention the oxygen concentration of the measuring gas can be detected by varying the reference voltage based on a predetermined mutual relationship between the electromotive force of the oxygen concentration cell at a predetermined oxygen concentration in the diffusion chamber and the amount of the pumping current, without the use of a reference gas or air. Accordingly, an air passageway communicating to the atmosphere need not be considered in the design of the device so that wide freedom in design is obtained.

Further, since the air passageway communicating to the atmosphere is not required, simplification of the device, and hence, decreased cost, can be considered. Moreover, the detecting means can be miniaturized.

Furthermore, as the oxygen concentration of the measuring gas can be detected by the abovementioned manner, the life of the detecting means can be prolonged by arranging means to compensate the voltage drop of the oxygen pump due to an increase of the surface resistance thereof due to aging.

Additionally, the desired relationship between the gain of the PI controller and the current amount of the pumping current can be established outside the oscillation region, and along the oscillation region so that the oscillating phenomena can be suppressed over a wide range of the current amount of the pumping current and hence, the range of measurement for the oxygen concentration can be widened.

What is claimed is:

1. An oxygen analyzer comprising:

an oxygen sensing element comprising a diffusion chamber in which a measurement gas diffuses and detecting means including an oxygen concentration cell and an oxygen pump surrounding said diffusion chamber;

setting voltage means for setting a reference voltage to which is compared an electromotive force produced by said oxygen concentration cell; and control means for controlling an amount of pumping current applied to said oxygen pump based on a deviation between said reference voltage and said electromotive force, said control means detecting an oxygen concentration of said measurement gas based on a predetermined relationship between oxygen concentration and said amount of pumping current;

wherein the setting voltage means sets said reference voltage by detecting said amount of pumping current applied to said oxygen pump or a control signal for controlling said pumping current, and setting the reference voltage at an electromotive force value corresponding to said amount of pumping current or said control signal based on a predetermined relationship between pumping current or control signal and electromotive force measured using a calibration gas having a known oxygen concentration, such that said reference voltage is varied relatively when the amount of pumping current or control signal is varied.

2. An oxygen analyzer according to claim 1, wherein the reference voltage is set to a value other than zero when the amount of pumping current or control signal is zero.

3. An oxygen analyzer comprising:

an oxygen sensing element comprising a diffusion chamber in which a measurement gas diffuses and detecting means including an oxygen concentration cell and an oxygen pump surrounding said diffusion chamber;

setting voltage means for setting a reference voltage to which is compared an electromotive force produced by said oxygen concentration cell; and control means for controlling an amount of pumping current applied to said oxygen pump, said control means comprising a proportional operation circuit and an integration operation circuit for providing a control signal for controlling the current amount applied to said oxygen pump based on a deviation between said reference voltage and said electromotive force; and means for decreasing the proportional gain of the proportional operation circuit based on the amount of pumping current applied to said oxygen pump;

wherein the setting voltage means sets said reference voltage by detecting said amount of pumping current applied to said oxygen pump or a control signal for controlling said pumping current, and setting the reference voltage at an electromotive force value corresponding to said amount of pumping current or said control signal based on a predetermined relationship between pumping current or control signal and electromotive force measured using a calibration gas having a known oxygen concentration, such that said reference voltage is varied relatively when the amount of pumping current or control signal is varied.

4. An oxygen analyzer according to claim 3, wherein said means for decreasing the proportional gain comprises at least one cadmium resistor arranged in a feedback circuit of an amplifying stage of said proportional operation circuit, and at least one photodiode optically coupled to said at least one cadmium resistor and supplied with current substantially proportional to the current applied to said oxygen pump.

5. An oxygen analyzer according to claim 3, wherein said means for decreasing the proportional gain of the proportional operation circuit are arranged between the proportional operation circuit and said integration operation circuit, said circuits being arranged in series, and said means being formed as a divider circuit to divide an output of the proportional operation circuit by an output of the integrating operation circuit and to supply the output to said integrating operation circuit.

* * * * *